United States Patent
Sugahara et al.

(10) Patent No.: US 9,576,380 B2
(45) Date of Patent: Feb. 21, 2017

(54) IMAGE DISPLAY DEVICE, IMAGE DISPLAY METHOD, MEDICAL IMAGE DIAGNOSTIC DEVICE, MEDICAL IMAGE DIAGNOSTIC METHOD, MEDICAL IMAGE DIAGNOSTIC SYSTEM, DATA PREPARATION DEVICE, DATA PREPARATION METHOD, AND NON-TRANSITORY RECORDING MEDIUM

(71) Applicant: FUJIFILM Corporation, Tokyo (JP)

(72) Inventors: Masataka Sugahara, Kanagawa (JP); Akira Hasegawa, San Jose, CA (US)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 14/796,560

(22) Filed: Jul. 10, 2015

(65) Prior Publication Data
US 2015/0348293 A1 Dec. 3, 2015

Related U.S. Application Data

(63) Continuation of application No. PCT/JP2013/084025, filed on Dec. 19, 2013.
(Continued)

(51) Int. Cl.
*G09G 5/00* (2006.01)
*G06K 9/00* (2006.01)
(Continued)

(52) U.S. Cl.
CPC .............. *G06T 11/008* (2013.01); *A61B 6/025* (2013.01); *A61B 6/032* (2013.01); *A61B 6/461* (2013.01); *A61B 6/466* (2013.01); *A61B 6/502* (2013.01); *A61B 6/5211* (2013.01); *A61B 6/5235* (2013.01); *G06T 1/0007* (2013.01); *G06T 7/0012* (2013.01); *G06T 11/60* (2013.01); *A61B 6/0414* (2013.01); *A61B 6/4417* (2013.01);
(Continued)

(58) Field of Classification Search
CPC ........ G06T 11/60; G06T 7/0012; A61B 6/032; A61B 6/025
USPC ...... 345/619; 382/128, 131; 600/425; 378/4, 378/21–27
See application file for complete search history.

(56) References Cited

U.S. PATENT DOCUMENTS

2004/0228434 A1 11/2004 Tsujii
2005/0285812 A1 12/2005 Shimayama et al.
(Continued)

FOREIGN PATENT DOCUMENTS

JP 63-57030 A 3/1988
JP 10-305015 A 11/1998
(Continued)

OTHER PUBLICATIONS

Translation of Written Opinion, Written Opinion in Japanese, Translation of International Search Report and International Search Report in Japanese for PCT/JP2013/084025, all dated Jan. 28, 2014, 16 pages in English and Japanese.
(Continued)

*Primary Examiner* — Ke Xiao
*Assistant Examiner* — Andrew Shin
(74) *Attorney, Agent, or Firm* — Sughrue Mion, PLLC

(57) ABSTRACT

In the present invention, in a case where a display unit is capable of displaying either multiple tomographic images or at least one plain image of a subject, a display control unit switches the display on the display unit to the display of tomographic images in sequence or to the display of a plain image.

13 Claims, 7 Drawing Sheets

Related U.S. Application Data

(60) Provisional application No. 61/751,533, filed on Jan. 11, 2013.

(51) Int. Cl.
| | | |
|---|---|---|
| *A61B 5/05* | (2006.01) | |
| *A61B 6/00* | (2006.01) | |
| *G06T 11/00* | (2006.01) | |
| *A61B 6/03* | (2006.01) | |
| *G06T 1/00* | (2006.01) | |
| *G06T 7/00* | (2006.01) | |
| *G06T 11/60* | (2006.01) | |
| *A61B 6/02* | (2006.01) | |
| *A61B 6/04* | (2006.01) | |

(52) U.S. Cl.
CPC ............... *A61B 6/469* (2013.01); *A61B 6/486* (2013.01); *A61B 6/488* (2013.01); *G06T 2200/04* (2013.01); *G06T 2207/10072* (2013.01); *G06T 2207/30068* (2013.01); *G06T 2210/41* (2013.01)

(56) References Cited

U.S. PATENT DOCUMENTS

| | | |
|---|---|---|
| 2006/0098855 A1 | 5/2006 | Gkanatsios et al. |
| 2009/0123052 A1 | 5/2009 | Ruth et al. |
| 2013/0079630 A1* | 3/2013 | Horiike ................ A61B 5/0066 |
| | | 600/425 |

FOREIGN PATENT DOCUMENTS

| | | |
|---|---|---|
| JP | 2004-086802 A | 3/2004 |
| JP | 2004-337289 A | 12/2004 |
| JP | 2006-006435 A | 1/2006 |
| JP | 2006-110208 A | 4/2006 |
| JP | 2007-130487 A | 5/2007 |
| JP | 2009-192384 A | 8/2009 |
| JP | 2012-512669 A | 6/2012 |

OTHER PUBLICATIONS

International Preliminary Report on Patentability and Written Opinion, mailed Jul. 23, 2015, issued in corresponding International Application No. PCT/JP2013/084025, 8 pages in English.
International Search Report for PCT/JP2013/084025 dated Jan. 28, 2014.

* cited by examiner

IMAGE DISPLAY DEVICE, IMAGE DISPLAY METHOD, MEDICAL IMAGE DIAGNOSTIC DEVICE, MEDICAL IMAGE DIAGNOSTIC METHOD, MEDICAL IMAGE DIAGNOSTIC SYSTEM, DATA PREPARATION DEVICE, DATA PREPARATION METHOD, AND NON-TRANSITORY RECORDING MEDIUM

CROSS-REFERENCE TO RELATED APPLICATIONS

This application is a Continuation of International Application No. PCT/JP2013/084025 filed on Dec. 19, 2013, which is based upon and claims the benefit of priority from provisional Patent Application No. U.S. Ser. No. 61/751,533 filed on Jan. 11, 2013, the contents all of which are incorporated herein by reference.

TECHNICAL FIELD

The present invention relates to an image display apparatus and an image display method for displaying a tomographic image or a plain image of a target object on a display unit, and a non-transitory recording medium storing a program for displaying such an image.

The present invention also is concerned with a medical image diagnosing apparatus and a medical image diagnosing method for generating a tomographic image using projected images of a target object, and displaying the generated tomographic image or a plain image on a display unit.

The present invention further relates to a medical image diagnosing system for imaging a target object in order to acquire projected images and a plain image thereof, generating a tomographic image using the acquired projected images, and displaying the generated tomographic image or the plain image on a display unit.

The present invention further is concerned with a data generating apparatus and a data generating method for acquiring a tomographic image and a plain image of a target object, and generating data for displaying the acquired tomographic image or the plain image on a display unit.

BACKGROUND ART

It has been a widely established practice to perform a tomosynthetic process by applying radiation to a target object (for example, a subject) from a plurality of respective different angles, detecting radiation that has passed through the target object with a radiation detector, converting the detected radiation into respective radiographic images (projected images), and processing the converted projected images in order to reconstruct a tomographic image at a desired sectional position in the target object. (See, for example, Japanese Laid-Open Patent Publication No. 2007-130487, Japanese Laid-Open Patent Publication No. 2009-192384, and Japanese Laid-Open Patent Publication No. 2012-512669 (PCT)).

The tomosynthetic process may be combined with a plain image capturing process for applying radiation to a target object from an angle (0°) in front of the target object, detecting radiation that has passed through the target object with a radiation detector, and converting the detected radiation into a radiographic image (plain image). Acquisition of such a plain image is not limited to acquisition by a plain image capturing process, which is carried out separately from the tomosynthetic process. For example, the tomosynthetic process may include, as a portion thereof, a process for producing a projected image, which is acquired by applying radiation to a target object from an angle of 0° as a plain image, or a process for generating a pseudo-plain image based on respective tomographic images at a plurality of sectional positions.

For displaying each of the acquired tomographic images and the plain image on an image display device, it has heretofore been customary to provide the image display device with a single display unit having two display areas on a screen thereof, or two display units having respective display areas on screens thereof, and to successively display the tomographic images in one of the display areas, while at the same time displaying the plain image in the other display area. Successively displaying tomographic images refers to displaying the tomographic images at respective sectional positions successively one after another, to thereby display a pseudo-three-dimensional image (hereinafter also referred to as a "reconstructed image") of the target object, which is reconstructed from the tomographic images.

SUMMARY OF INVENTION

Heretofore, as described above, the two-dimensional (2D) plain image and the three-dimensional (3D) reconstructed image (tomographic images) are simultaneously displayed in different display areas on the screen of a single display unit, or in different display areas on respective screens of two display units.

Consequently, the operator (a doctor, for example) who views the screen or screens needs to compare the images, extract an irregularity such as a lesion, and diagnose the irregularity (for example, interpret and diagnose the extracted irregularity to see whether it is part of a lesion or tissue). The operator, therefore, has to work under an increased burden such as increased eye strain.

The present invention has been made in view of the above problems. An object of the present invention is to make it possible to display, for comparison, a 2D plain image and a 3D reconstructed image (tomographic images) on a screen so that the face or the eyes of an operator do not have to move.

Another object of the present invention is to make it possible for an operator to extract an irregularity with ease from a 2D plain image and a 3D reconstructed image, which are displayed for comparison.

In order to achieve the above objects, the present invention has the following arrangements.

[1] With an image display apparatus and an image display method according to the present invention, a display unit is capable of displaying a plurality of tomographic images, or at least one plain image of a target object. A display controller switches the display on the display unit to the display of tomographic images in sequence, or to the display of a plain image.

With a medical image diagnosing apparatus and a medical image diagnosing method according to the present invention, a tomographic image generator generates a plurality of tomographic images using a plurality of projected images captured of a target object, a display unit is capable of displaying the tomographic images or at least one plain image captured of the target object, and a display controller is capable of switching the display on the display unit to the display of tomographic images in sequence or to the display of a plain image.

A medical image diagnosing system according to the present invention includes an image capturing apparatus configured to acquire a plurality of projected images captured of a target object and at least one plain image captured of the target object, and the medical image diagnosing apparatus, as described above, configured to acquire the projected images and the plain image from the image capturing apparatus.

With a data generating apparatus and a data generating method according to the present invention, a display controller is capable of displaying a plurality of tomographic images or at least one plain image of a target object on a display unit, a data generator generates data in which a plain image is inserted per a prescribed number of tomographic images, and in case that the display controller is supplied with the data, the display controller switches the display on the display unit to the display of tomographic images in sequence or to the display of a plain image, based on the data.

A program according to the present invention enables a computer to function as a display unit capable of displaying a plurality of tomographic images or at least one plain image of a target object, and a display controller configured to switch the display on the display unit to the display of tomographic images in sequence or to the display of a plain image. Further, according to the present invention, the program is stored in a non-transitory recording medium.

According to the inventions described above, the display of a plurality of tomographic images in sequence (the display of a reconstructed image) switches to the display of a plain image, or the display of a plain image switches to the display of tomographic images at any desired timing on the screen of the display unit. Consequently, according to the present invention, a tomographic image and a plain image are not displayed simultaneously on the same screen, thereby making it possible to display each of the tomographic image and the plain image for comparison on one screen.

Immediately after the display on the screen has been switched, due to an afterimage effect, the operator perceives the image that was displayed immediately before switching of the display as remaining. Therefore, in a case where the operator views an image displayed on the screen immediately after switching of the display, the operator is capable of comparing the image and the image immediately before switching of the display, which is perceived due to an afterimage effect.

Therefore, the operator is capable of comparing a two-dimensional plain image and a three-dimensional reconstructed image (tomographic images) with each other without moving the face or the eyes, and thus the operator is subjected to a reduced working burden. The operator also can easily extract irregularities based on the difference (differential) between the image (afterimage) displayed immediately before switching of the display, and the image displayed immediately after switching of the display. More specifically, the operator is able to easily identify irregularities and to pay attention to that which is included within a plain image, as to which tomographic image the irregularities are included in, which sectional position the irregularities exist in, and what the shape and concentration of the irregularities are, etc.

[2] The image display apparatus and the medical image diagnosing apparatus described above further include a switching determiner configured to determine whether to switch the display on the display unit. The display controller controls the display unit based on a determined result from the switching determiner. Thus, the display controller can switch the display on the display unit at an appropriate timing.

[3] In [2] referred to above, in case that the switching determiner determines to switch the display on the display unit, the display controller controls the display unit to display an image, which is different in kind from the image displayed on the display unit, instead of the image displayed on the display unit. Therefore, it is possible to efficiently switch from the display of tomographic images in sequence to the display of a plain image, or from the display of a plain image to the display of tomographic images in sequence.

[4] In [3] referred to above, in case that a tomographic image is displayed on the display unit, the display controller may control the display unit to display a sequence of a plain image, a tomographic image, and a plain image, instead of the tomographic image displayed on the display unit. In this manner, the operator is capable of comparing a plain image and a tomographic image with each other due to an afterimage effect, and can efficiently ascertain whether or not irregularities that correspond to irregularities included within the tomographic image (afterimage) exist in the plain image, and to confirm how such corresponding irregularities are included within the plain image. In other words, the operator can easily make a comparative observation as to how irregularities that are found in a tomographic image are included within a plain image, and can ascertain the shape and concentration of such irregularities.

[5] In [3] referred to above, in case that a plain image is displayed on the display unit, the display controller may control the display unit to display a sequence of a tomographic image, a plain image, and a tomographic image, instead of the plain image displayed on the display unit. In this case, the operator can also compare a plain image and a tomographic image with each other due to an afterimage effect, and can efficiently ascertain whether or not irregularities included within the plain image (afterimage) exist in the tomographic image, and can confirm how the corresponding irregularities are included within the tomographic image. In other words, the operator can easily make a comparative observation as to how irregularities that are found in a plain image are included within a tomographic image, and can ascertain the shape and concentration of such irregularities.

[6] In [5] referred to above, using a tomographic image, which is displayed in a preceding order to the plain image displayed on the display unit, the display controller may control the display unit to display a sequence of the tomographic image, a plain image, and a tomographic image, instead of the plain image displayed on the display unit. According to this feature, it is possible to more efficiently display a plain image and a tomographic image for comparison, as well as to search for and confirm irregularities in the tomographic image.

[7] The image display apparatus and the medical image diagnosing apparatus described above may further include a cancellation instructing unit configured to instruct the display controller to cancel the display on the display unit. In this case, the display controller may cancel the display on the display unit in response to instructions from the cancellation instructing unit, and the switching determiner may determine whether or not to switch the display on the display unit that has been canceled by the display controller. Consequently, using the cancellation instructing unit, the operator can instruct the display controller to cancel the display on the display unit and switch the display at any desired timing.

In response to instructions from the cancellation instructing unit, the switching determiner may determine to immediately switch the display on the display unit, or may determine to switch the display on the display unit after the elapse of a predetermined time. In either case, in response to instructions from the cancellation instructing unit, the switching determiner can perform a determining process for switching the display on the display unit at any appropriate timing.

[8] In case that the display controller controls the display unit to display tomographic images in sequence, the display controller may control the display unit to display a plain image each time that the display unit displays a prescribed number of tomographic images in sequence. In this manner, the screen of the display unit automatically switches between tomographic images and a plain image each time that a prescribed number of tomographic images are displayed. As a result, the operator can more efficiently compare the tomographic image and the plain image with each other and extract irregularities. In other words, the operator can efficiently make a comparative observation as to how irregularities that are found in a tomographic image are included within a plain image, and a comparative observation as to how irregularities that are found in a plain image are included within a tomographic image.

[9] In [8] referred to above, the display controller may control the display unit to display tomographic images in sequence, using data in which a plain image is inserted per each prescribed number of tomographic images. Thus, controlling the switching of the display on the display unit can be simplified. The data may be generated in advance by the data generating apparatus and the data generating method described above.

[10] The display controller preferably controls the display unit to display the tomographic images and the plain image at substantially the same scale. Therefore, movement of the face and eyes of the operator can be reduced, so that the operator is subjected to a reduced working burden. Further, since the images are displayed at the same scale, the operator is capable of easily comparing irregularities such as lesions or the like to which attention should be focused on in the plain image and in the tomographic images, as to what size and concentration the irregularities have.

[11] The display controller may control the display unit to display the tomographic images in sequence after having controlled the display unit to display the plain image. Therefore, after the operator has extracted irregularities that are included within the plain image by viewing the plain image, the operator can confirm whether or not a tomographic image exists that includes the extracted irregularities by viewing the tomographic images.

[12] The tomographic images preferably are displayed in sequence in a cine-display mode.

According to the present invention, since the display controller switches the display on the display unit to the display of tomographic images in sequence or the display of a plain image, a 2D plain image and a 3D reconstructed image (respective tomographic images) can be displayed for comparison on the screen in such a manner that the face or eyes of the operator do not have to move. In case that the display on the display unit is switched, the image immediately before switching of the display remains as an afterimage due to an afterimage effect, whereby the operator can easily extract particular targets (irregularities) by viewing the image immediately after switching of the display.

The above objects, features, and advantages of the present invention will easily be understood from an embodiment to be described below with reference to the accompanying drawings.

DESCRIPTION OF EMBODIMENTS

Figure 1:
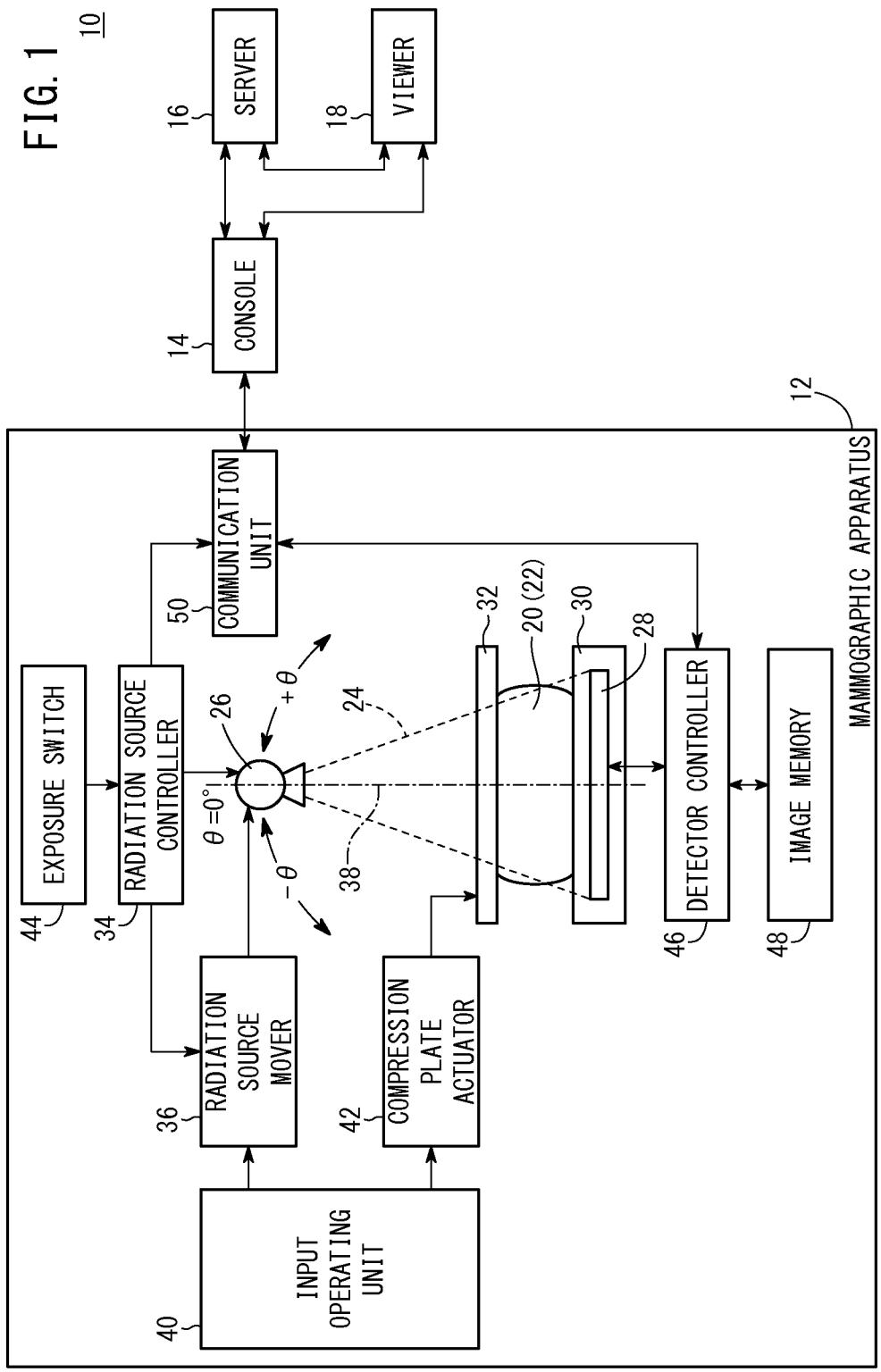
FIG. 1 is a block diagram of a medical image diagnosing system according to an embodiment of the present invention.

A preferred embodiment of the present invention will be described in detail below with reference to FIGS. 1 through 7B.

[Configuration of the Embodiment]

First, a medical image diagnosing system 10 according to the present embodiment will be described below with reference to FIGS. 1 through 3.

The medical image diagnosing system 10 comprises a mammographic apparatus 12 as an image capturing apparatus, a console 14 (image display apparatus, medical image diagnosing apparatus, data generating apparatus, computer) for controlling the mammographic apparatus 12, a server 16 that serves as a medical image information system (PACS) for centralized control over various items of information, and a viewer 18 (image display apparatus, medical image diagnosing apparatus, data generating apparatus, computer) that is used by the doctor in order to interpret and diagnose images displayed thereon.

The mammographic apparatus 12 applies radiation 24 to a breast 22 of a subject 20 as a target object, thereby acquiring radiographic images (projected images, a plain image) of the breast 22.

More specifically, the mammographic apparatus 12 has a radiation source 26 for emitting radiation 24, an image capturing table 30 for placement of the breast 22 thereon, the image capturing table 30 housing a solid-state detector 28 therein, and a compression plate 32 disposed between the radiation source 26 and the image capturing table 30. The compression plate 32 is displaceable toward the image capturing table 30 to compress and hold the breast 22 in cooperation with the image capturing table 30. The solid-state detector 28 converts radiation 24 that has passed through the breast 22 into a radiation image.

The radiation source 26 is energizable by a radiation source controller 34. The radiation source 26 also can be actuated by a radiation source mover 36 for angular movement in a +θ direction (clockwise in FIG. 1) or a −θ direction (counterclockwise in FIG. 1) with respect to the breast 22 about a vertical axis 38 that extends perpendicularly to the surface of the image capturing table 30 on which the breast 22 is placed. The vertical axis 38 extends in the direction of θ=0°. In FIG. 1, the radiation source 26 is illustrated as applying radiation 24 to the breast 22 while being disposed in a position of θ=0°, for example.

According to the present embodiment, in case that the radiation source 26 is disposed in a position of θ=0°, then in case that the radiation source 26, which is positioned in this manner, applies radiation 24 to the breast 22, the medical image diagnosing system 10 carries out a plain image capturing process in which radiation 24 that has passed through the breast 22 is converted into a radiographic image (plain image) by the solid-state detector 28. On the other hand, in case that the radiation source 26 is angularly moved in a +θ direction or a −θ direction by the radiation source mover 36 so as to be placed at a plurality of different angles, then in case that the radiation source 26, which is positioned in this manner, applies radiation 24 to the breast 22, the medical image diagnosing system 10 carries out a tomosynthetic image capturing process in which radiation 24 that has passed through the breast 22 from different angles is converted into respective radiographic images (projected images) by the solid-state detector 28.

In the plain image capturing process, the radiation source 26 applies radiation 24 to the breast 22, which is of a higher dose than in the tomosynthetic image capturing process, and the solid-state detector 28 acquires a plain image from the radiation 24 that has passed through the breast 22. In the tomosynthetic image capturing process, the radiation source 26 that is disposed in the position θ=0° may apply radiation 24, which is of a low dose, to the breast 22, and the solid-state detector 28 may convert the radiation 24 that has passed through the breast 22 into a projected image, thereby acquiring a plain image at a lower dose than in the plain image capturing process.

The mammographic apparatus 12 also has an input operating unit 40, a compression plate actuator 42, an exposure switch 44, a detector controller 46, an image memory 48, and a communication unit 50.

The compression plate actuator 42 moves the compression plate 32, which is disposed between the radiation source 26 and the image capturing table 30, toward and away from the image capturing table 30. The input operating unit 40 is an input operating unit such as an operating button or a touch panel on the mammographic apparatus 12. In response to an operation carried out on the input operating unit 40 by the doctor or radiological technician, the compression plate actuator 42 moves the compression plate 32 so as to compress the breast 22 that is placed on the image capturing table 30, or to release the breast 22 from a compressed state. In response to an operation carried out on the input operating unit 40 by the doctor or radiological technician, the radiation source mover 36 moves the radiation source 26 to a desired angle.

The exposure switch 44 is a switch that is operated by the doctor or radiological technician. In a case where the doctor or radiological technician presses the exposure switch 44, the radiation source controller 34 energizes the radiation source 26 so as to enable the radiation source 26 to start emitting radiation 24. The detector controller 46 controls the solid-state detector 28 in order to acquire radiographic images (projected images, a plain image) therefrom, and stores the acquired radiographic images in the image memory 48.

The communication unit 50 sends various signals or information to or receives various signals or information from the console 14. For example, the communication unit 50 sends a radiographic image, which the detector controller 46 has read from the image memory 48, to the console 14. The communication unit 50 receives image capturing conditions for a radiographic image capturing process to be performed on the breast 22 from the console 14, and outputs the received image capturing conditions to the radiation source controller 34.

Figure 2:
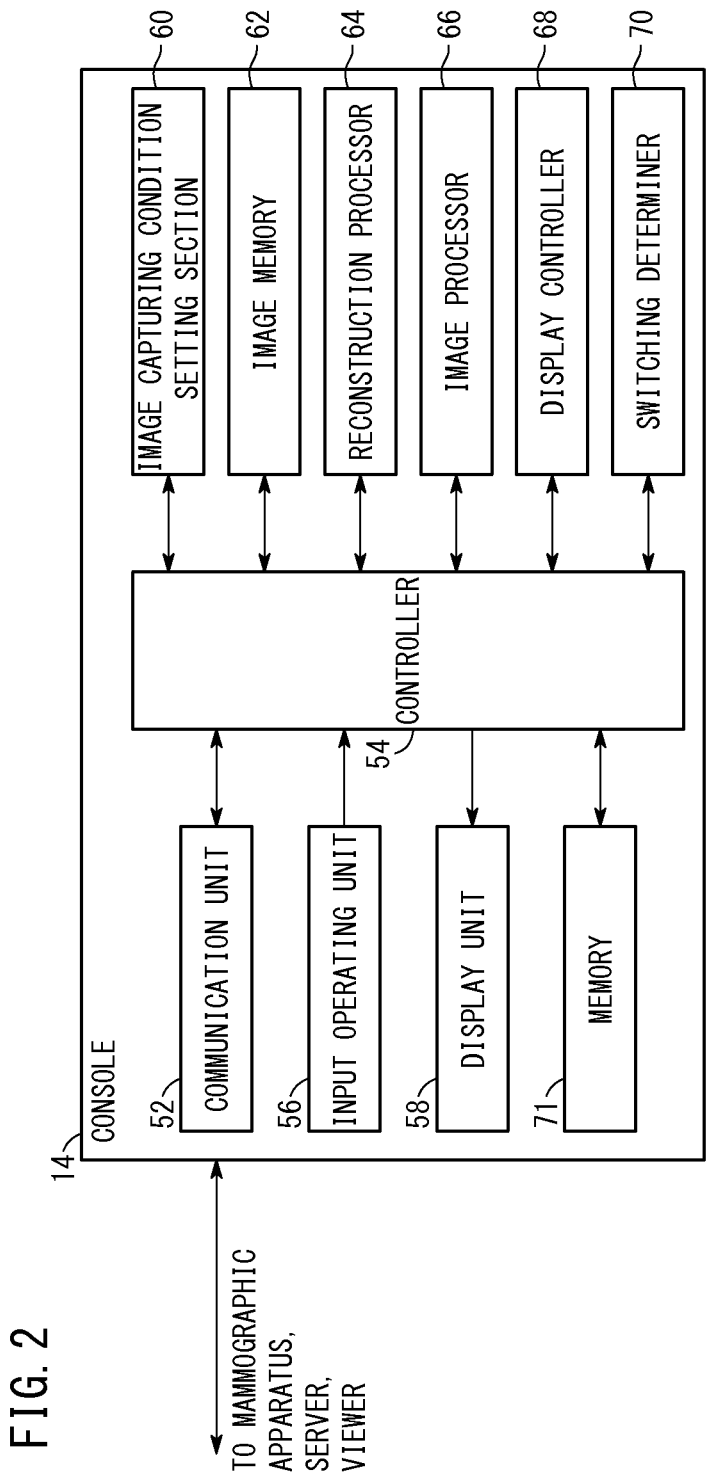
FIG. 2 is a block diagram of a console shown in FIG. 1.

As shown in FIG. 2, the console 14 has a communication unit 52, a controller 54, an input operating unit 56 (cancellation instructing unit), a display unit 58, an image capturing condition setting section 60, an image memory 62, a reconstruction processor 64 (tomographic image generator), an image processor 66 (data generator), a display controller 68, a switching determiner 70, and a memory 71 (recording medium).

The controller 54 controls various parts of the console 14 by reading and executing programs stored in the memory 71, which is a recording medium such as a ROM, a hard disk, a CD-ROM, or the like. The communication unit 52 sends various signals or information to or receives various signals or information from the mammographic apparatus 12, the server 16, and the viewer 18 (see FIG. 1) under the control of the controller 54. The input operating unit 56 is an input operating unit such as an operating button, a touch panel, or a mouse wheel or the like, which can be operated by the doctor or radiological technician. The display unit 58 is a display device such as a display panel or the like, which is capable of displaying various items of information.

The image capturing condition setting section 60 sets image capturing conditions concerning radiographic image capturing processes (a tomosynthetic image capturing process, a plain image capturing process) for applying radiation 24 from the radiation source 26 to the breast 22, converting radiation 24 that has passed through the breast 22 into a radiographic image with the solid-state detector 28, and acquiring the radiographic image. For the plain image capturing process, the image capturing conditions include a tube voltage of the radiation source 26, an mAs value (the product of a tube current and an irradiation time for the radiation 24), an image capturing angle (θ=0°), and information concerning the subject 20 (a region to be imaged). For the tomosynthetic image capturing process, the image capturing conditions include a tube voltage of the radiation source 26, an mAs value, an image capturing sequence (a direction of motion of the radiation source 26 during the image capturing process, an image capturing angle θ), and information concerning the subject 20.

The image capturing conditions are set by the doctor or radiological technician who operates the input operating unit 56, while viewing order information that is displayed on the display unit 58 after the communication unit 52 has acquired the order information from the server 16. The order information includes information concerning the mammographic apparatus 12 that is used in the image capturing process, a region to be imaged of the subject 20, an image capturing method, etc., in addition to subject information for identifying the subject 20, such as the name, age, gender, etc., of the subject 20. The order information is stored in the image capturing condition setting section 60.

The image memory 62 stores various kinds of images including radiographic images (projected images, plain images) received through the communication unit 52.

The reconstruction processor 64 reads a plurality of projected images stored in the image memory 62, and performs a known reconstructing process on each of the read projected images in order to generate tomographic images at respective sectional positions (vertical positions along the vertical axis 38 shown in FIGS. 1 and 6A) of the breast 22. The generated respective tomographic images are stored in the image memory 62. The reconstruction processor 64 also is capable of generating projected images at θ=0° (pseudo-plain images) using the generated respective tomographic images, and storing the generated pseudo-plain images in the image memory 62.

Unless otherwise noted, the acquisition of a plain image according to a plain image capturing process, which is carried out separately from a tomosynthetic image capturing process, will be described below.

The image processor 66 reads respective tomographic images and plain images that are stored in the image memory 62, and performs a predetermined image processing routine on the read images for displaying the read images on the display unit 58. The respective tomographic images and the plain images that have been processed are also stored in the image memory 62. In order to display the plain images on the display unit 58 while the respective tomographic images are successively displayed thereon, as described later, the image processor 66 also is capable of generating image display data in which a plain image is inserted after every prescribed number of respective tomographic images. Such image display data also are stored in the image memory 62.

The display controller 68 controls the display unit 58 in order to display various items of information on the screen of the display unit 58.

More specifically, the display controller 68 reads respective tomographic images and plain images stored in the image memory 62, and successively displays the read respective tomographic images on the display unit 58. The display controller 68 also displays the read plain images on the display unit 58. The display controller 68 also is capable of temporarily disabling the successive display of respective tomographic images on the display unit 58, and switching to the display of a plain image on the display unit 58, or of temporarily disabling the display of a plain image on the display unit 58, and switching to the successive display of respective tomographic images.

According to instructions from the switching determiner 70, the display controller 68 may switch between displaying images on the display unit 58, or may insert and display a read plain image on the display unit 58 per each of a prescribed number of read tomographic images. Alternatively, in case that the image display data referred to above are stored in the image memory 62, the display controller 68 may read the image display data from the image memory 62, and display the read image display data on the display unit 58.

Figure 6A:
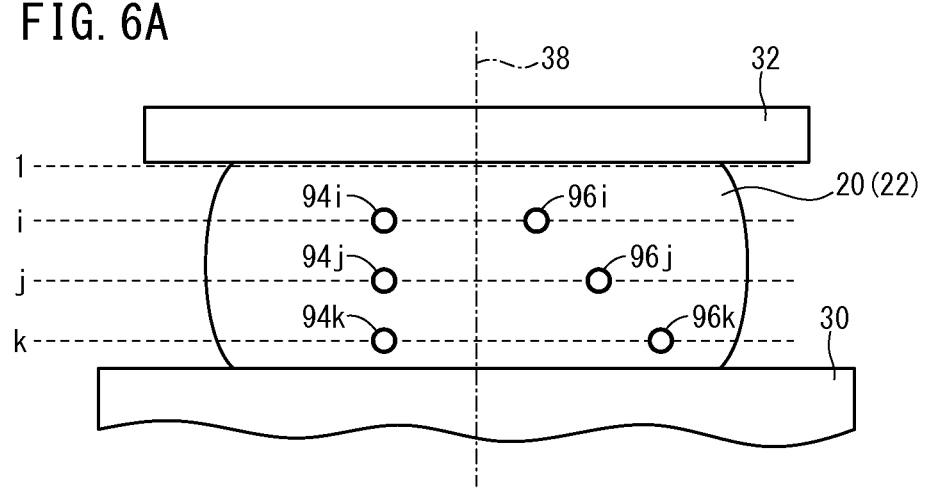
FIG. 6A is a view showing a breast that has been placed in a compressed state.

Successive display of respective tomographic images refers to displaying tomographic images at a plurality of sectional positions one after another on the screen of the display unit 58, in a sequence of sectional positions (a sequence along a direction from the compression plate 32 toward the image capturing table 30 in FIGS. 1 and 6A, or a sequence along the opposite direction), thereby displaying a pseudo-three-dimensional image (reconstructed image) of the breast 22 that is reconstructed from the tomographic images.

According to the present embodiment, the tomographic images preferably are displayed successively in a cine-display mode (an animated display of a reconstructed image). More specifically, the cine-display mode covers the following cases (1) through (3):

(1) Displaying respective tomographic images that the display controller 68 has read from the image memory 62, automatically one after another on the display unit 58 in a sequence of sectional positions thereof.

(2) Displaying respective tomographic images, which are automatically displayed one after another on the display unit 58, using image display data that the display controller 68 has read from the image memory 62.

(3) Displaying tomographic images that the display controller 68 has read from the image memory 62, such that after a tomographic image at a first sectional position has been displayed on the display unit 58, in a case where the doctor operates the input operating unit 56 (e.g., in a case where the doctor operates the mouse wheel) while viewing the tomographic image displayed on the display unit 58, the display controller 68 successively displays respective tomographic images on the display unit 58 according to operations of the input operating unit 56.

In addition to displaying tomographic images one after another from the tomographic image at the first sectional position toward the tomographic image at the last sectional position, and displaying tomographic images one after another from the tomographic image at the last sectional position toward the tomographic image at the first sectional position, the cine-display mode also covers a situation of displaying a plurality of tomographic images one after another within a range of desired sectional heights, and displaying a plurality of tomographic images within a range of desired sectional heights based on an operation made on the mouse wheel by the doctor.

For example, in case that the doctor spots an irregularity (target) such as a lesion or the like which the doctor is concerned about while viewing a tomographic image at any sectional position that is displayed on the display unit 58 in the cine-display mode, the doctor can operate the input operating unit 56 in order to instruct the display controller 68 to cancel the cine-display mode.

More specifically, based on instructions from the input operating unit 56, the display controller 68 temporarily cancels the cine-display mode on the display unit 58. On the basis of the instructions from the input operating unit 56, the switching determiner 70 determines whether or not it is necessary to switch from the cine-display mode on the display unit 58, and transmits the determined result to the display controller 68. In case that the determined result indicates that it is necessary to switch from the cine-display mode, the display controller 68 controls the display unit 58 in order to switch from the tomographic image that is currently displayed on the screen of the display unit 58 to a plain image that is different in kind from the tomographic image. In other words, according to the present embodiment, a 2D plain image is forcibly inserted and displayed on the display unit 58 during the cine-display mode. Consequently, the doctor can observe the plain image, which has switched from the tomographic image, to thereby confirm whether or not a lesion or the like depending on the target is included within the plain image.

As described above, the server 16 performs a centralized control over various items of information including order information, etc., and acquires and stores various images that are stored in the image memory 62 of the console 14.

Figure 3:
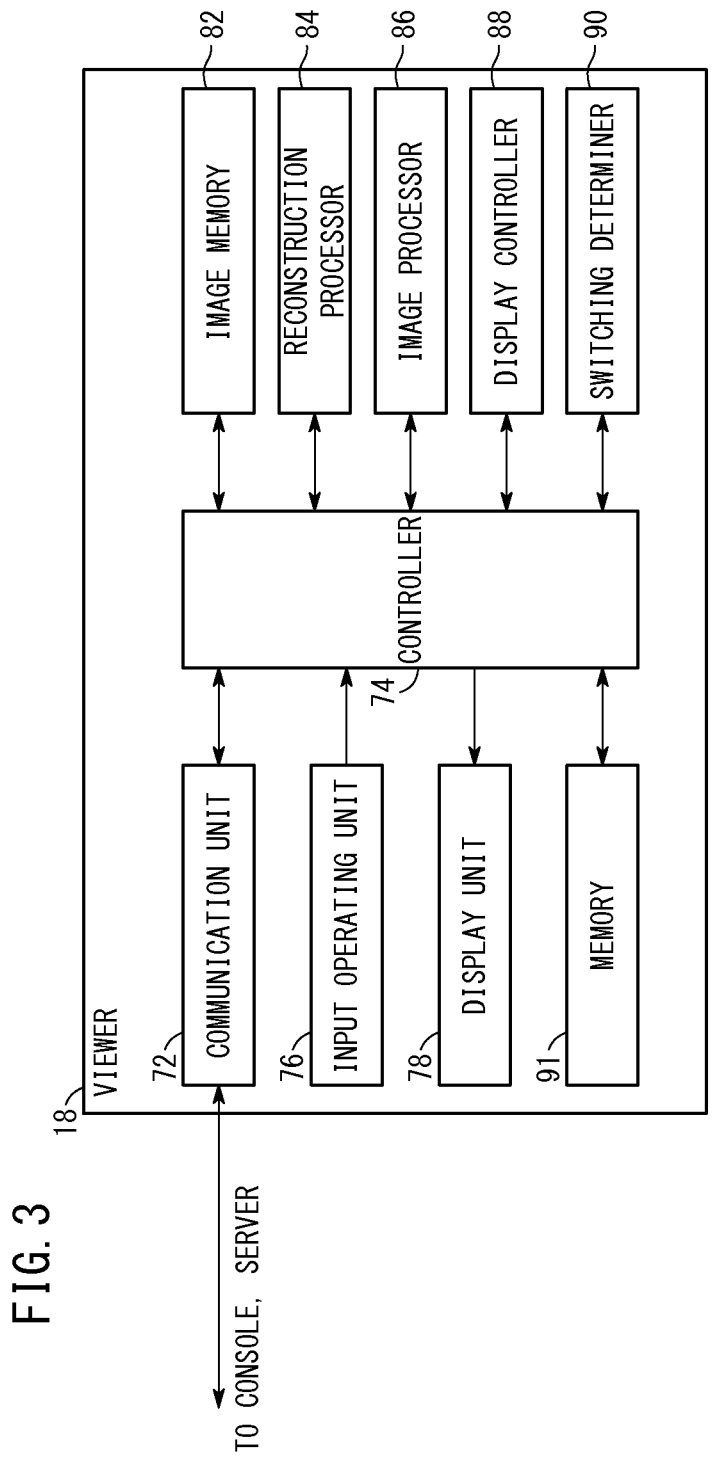
FIG. 3 is a block diagram of a viewer shown in FIG. 1.

As shown in FIG. 3, the viewer 18 has a communication unit 72, a controller 74, an input operating unit 76 (cancellation instructing unit), a display unit 78, an image memory 82, a reconstruction processor 84 (tomographic image generator), an image processor 86 (data generator), a display controller 88, a switching determiner 90, and memory 91 (recording medium). The viewer 18 is substantially similar in configuration to the console 14, except that the viewer 18 does not include the image capturing condition setting section 60 and does not control the mammographic apparatus 12.

More specifically, the communication unit 72, the controller 74, the input operating unit 76, the display unit 78, the image memory 82, the reconstruction processor 84, the image processor 86, the display controller 88, the switching determiner 90, and the memory 91 of the viewer 18 have the same functions as the communication unit 52, the controller 54, the input operating unit 56, the display unit 58, the image memory 62, the reconstruction processor 64, the image processor 66, the display controller 68, the switching determiner 70, and the memory 71 of the console 14. Descriptions of the above components of the console 14 are applicable to corresponding components of the viewer 18, in a case where the reference characters denoting the components of the console 14 are replaced with reference characters denoting the corresponding components of the viewer 18. Therefore, detailed description of the viewer 18 will be omitted.

Since the console 14 and the viewer 18 have substantially similar components, unless otherwise indicated, descriptions will be given below concerning the display of plain images or the cine-display mode on the display unit 58 of the console 14.

[Operations of the Embodiment]

The medical image diagnosing system 10 according to the present embodiment is configured as described above. Operations (an image display method, a medical image diagnosing method, and a data generating method) of the medical image diagnosing system 10 will be described below with reference to FIGS. 4 through 7B, and also with reference to FIGS. 1 through 3 as necessary.

In the description of such operations, it will primarily be assumed that the console 14 generates a plurality of tomographic images (a 3D reconstructed image) from a plurality of projected images, and the display unit 58 displays a 3D reconstructed image or a 2D plain image.

Figure 4:
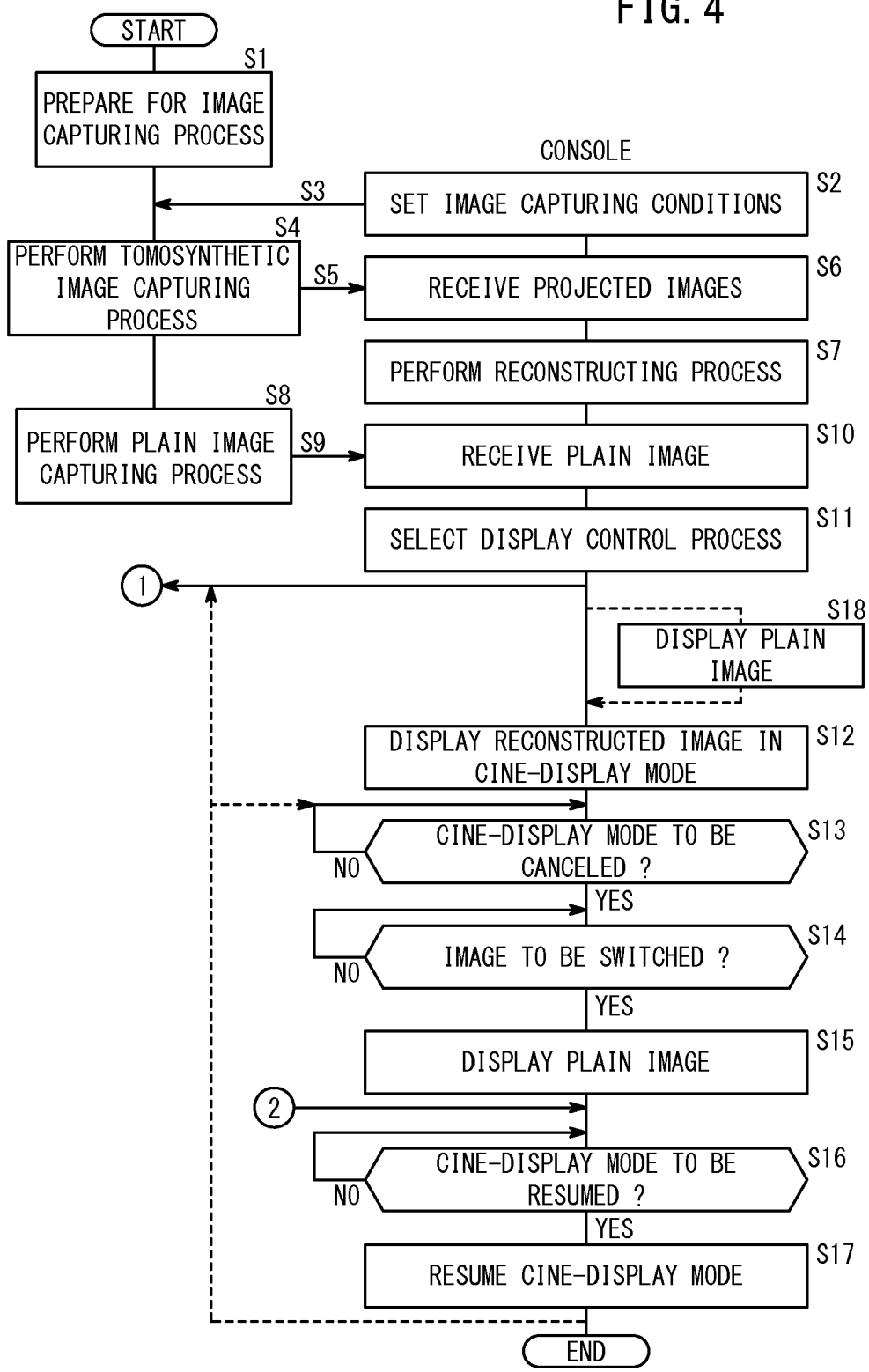
FIG. 4 is a flowchart of an operation sequence of the embodiment.
Figure 5:
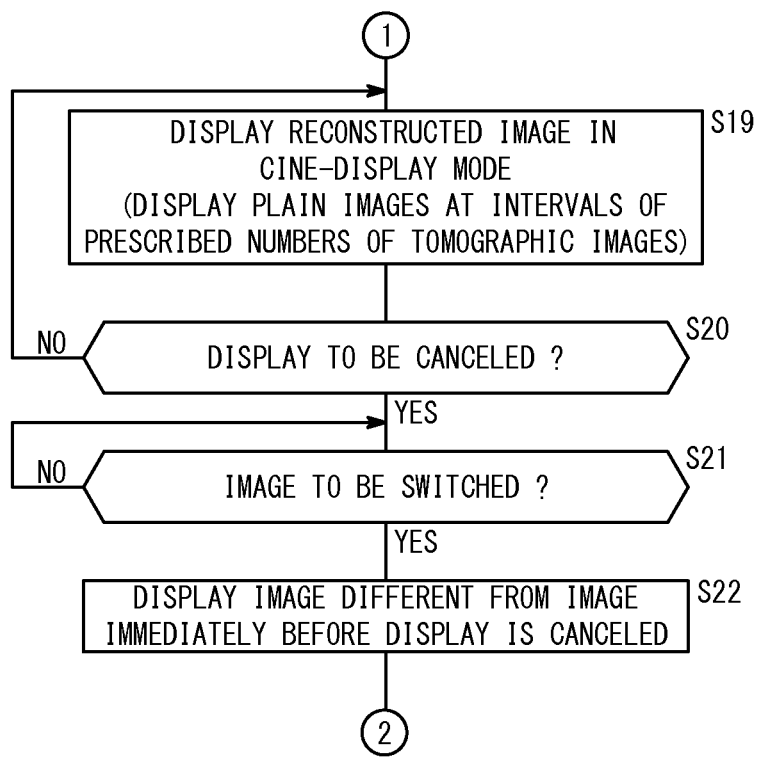
FIG. 5 is a flowchart of an operation sequence of the embodiment.

In step S1 of FIG. 4, first, the doctor or radiological technician places the breast 22 on the image capturing table 30. Then, in response to an operation carried out on the input operating unit 40 by the doctor or radiological technician, the compression plate actuator 42 moves the compression plate 32 toward the image capturing table 30, thereby causing the compression plate 32 and the image capturing table 30 to compress the breast 22, as shown in FIGS. 1 and 6A.

In FIG. 6A, sectional images denoted by 1 . . . i . . . j . . . k . . . for example, are illustrated, which correspond to tomographic images along the vertical axis 38 from the compression plate 32 toward the image capturing table 30. Targets 94$i$, 96$i$ such as lesions or the like exist at the ith sectional position, targets 94$j$, 96$j$ exist at the jth sectional position, and targets 94$k$, 96$k$ exist at the kth sectional position. The respective targets 94$i$ through 94$k$ are positioned at equal distances mutually along each of the sectional positions from the vertical axis 38, whereas the targets 96$i$ through 96$k$ are positioned at different positions mutually along each of the sectional positions from the vertical axis 38.

In the following step S2, the controller 54 of the console 14 receives order information from the server 16 through the communication unit 52, stores the order information in the image capturing condition setting section 60, and displays the order information on the display unit 58. The doctor or radiological technician operates the input operating unit 56 in order to enter a tube voltage, an mAs value, etc., while viewing the order information that is displayed on the screen of the display unit 58, thereby setting in the image capturing condition setting section 60 the image capturing conditions for radiographic image capturing processes (the tomosynthetic image capturing process, the plain image capturing process) to be carried out on the breast 22.

In step S3, in a case where the doctor or radiological technician presses the exposure switch 44, the radiation source controller 34 requests the console 14 through the communication unit 50 to send the image capturing conditions for the tomosynthetic image capturing process and the plain image capturing process. In response to the request from the radiation source controller 34, the controller 54 sends the image capturing conditions, which are set in the image capturing condition setting section 60, through the communication unit 52 to the mammographic apparatus 12. In a case where the communication unit 50 receives the image capturing conditions, the communication unit 50 outputs the image capturing conditions to the radiation source controller 34.

In step S4, the radiation source controller 34 energizes the radiation source 26 and the radiation source mover 36 in order to carry out the tomosynthetic image capturing process.

More specifically, the radiation source mover 36 moves the radiation source 26 in a direction according to the image capturing conditions, and as the radiation source 26 is placed at different angles, the radiation source 26 applies radiation 24 to the breast 22. Radiation 24 that has passed through the breast 22 is converted respectively into projected images by the solid-state detector 28. The detector controller 46 stores the respective projected images acquired by the solid-state detector 28 sequentially in the image memory 48.

After the tomosynthetic image capturing process has been performed, in step S5, the detector controller 46 sends the plurality of projected images stored in the image memory 48 through the communication unit 50 to the console 14.

Figure 7A:
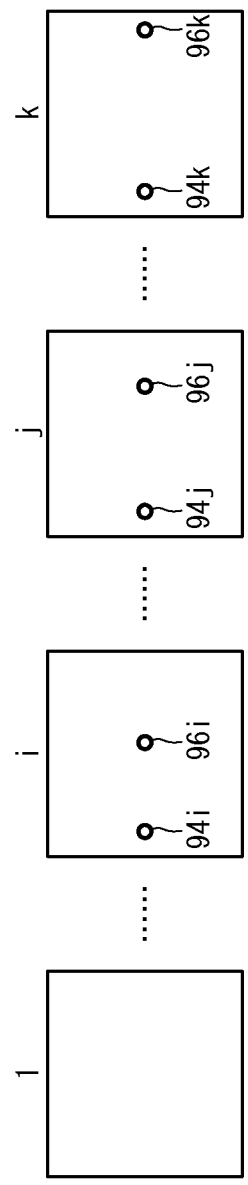
FIG. 7A is a diagram showing a manner in which tomographic images of the breast are displayed in a cine-display mode.

In step S6, the controller 54 receives the respective projected images through the communication unit 52, and temporarily stores the projected images in the image memory 62. In the following step S7, the reconstruction processor 64 reads the respective projected images that are stored in the image memory 62, and performs a known reconstruction process on each of the read projected images in order to generate tomographic images at a plurality of sectional positions along the vertical axis 38. The generated respective tomographic images are stored in the image memory 62. FIG. 7A shows the respective tomographic images at the sectional positions 1 . . . i . . . j . . . k . . . that are shown in FIG. 6A.

In step S8, after the tomosynthetic image capturing process has been carried out, the radiation source mover 36 moves the radiation source 26 to the position θ=0°, and the mammographic apparatus 12 performs the plain image capturing process, in which the radiation source 26 applies radiation 24 to the breast 22. In the plain image capturing process, radiation 24 is applied to the breast 22 at a higher dose than in the tomosynthetic image capturing process. Radiation 24 that has passed through the breast 22 is converted into a plain image by the solid-state detector 28, and the detector controller 46 stores the plain image, which is acquired by the solid-state detector 28, in the image memory 48.

Figure 6B:
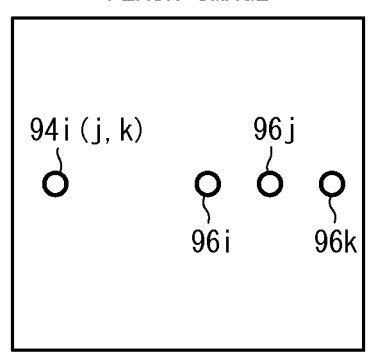
FIG. 6B is a diagram showing a plain image of the breast, which is displayed on a display unit.

FIG. 6B shows the plain image of the breast 22 that is shown in FIG. 6A, with all of the targets 94$i$ through 94$k$, and 96$i$ through 96$k$ included therein. The plain image is a projected image that is acquired in a case where the radiation source 26 is placed in the position θ=0°, and radiation 24 is applied therefrom to the breast 22. Therefore, the three targets 94i through 94k are displayed in overlapping positions, whereas the three targets 96i through 96k are displayed in mutually different positions.

In step S9, after the plain image capturing process has been carried out, the detector controller 46 sends the plain image that is stored in the image memory 48 through the communication unit 50 to the console 14.

In step S10, the controller 54 receives the plain image through the communication unit 52 and temporarily stores the plain image in the image memory 62. The image memory 62 stores therein a plurality of the projected images, a plurality of the tomographic images, and at least one plain image. The controller 54 reads all of the images that are stored in the image memory 62, and sends the read images through the communication unit 52 to the server 16 and the viewer 18. The server 16 stores the received images in a non-illustrated image memory, whereas the viewer 18 temporarily stores the received images in the image memory 82.

As described above, since it is possible to carry out a plain image capturing process as part of the tomosynthetic image capturing process, the processes of steps S8 through S10 are not required in case that a plain image capturing process is carried out in such a way. It also is possible to generate a pseudo-plain image using the respective tomographic images in step S7. In this case, the processes of steps S8 through S10 are not required either.

In step S11, the display controller 68 selects details of display control processes for controlling the display unit 58 to display a plurality of tomographic images and a single plain image that are stored in the image memory 62.

In other words, the display controller 68 controls the display unit 58 to display a plurality of tomographic images successively (to display a 3D reconstructed image in the cine-display mode), and also to display a single plain image. Furthermore, the display controller 68 performs a control process for switching from the display of a 3D reconstructed image in the cine-display mode to the display of a plain image on the display unit 58, or a control process for switching from the display of a plain image to the display of a 3D reconstructed image in the cine-display mode.

Depending on the type of images to be displayed on the display unit 58 or the method of switching between displayed images on the display unit 58, display control processes carried out on the display unit 58 by the display controller 68 are classified into the following processes (1) through (4) described below. Therefore, in step S11, the display controller 68 selects any one of the control processes (1) through (4). Any one of the control processes may be selected automatically by the display controller 68. Alternatively, details of the control processes may be displayed on the display unit 58, and a desired one of the control processes may be selected by the doctor who operates the input operating unit 56.

(1) First Control Process

A plurality of tomographic images are displayed successively on the screen of the display unit 58 (a 3D reconstructed image is displayed in the cine-display mode), and in case that there are switching instructions from the switching determiner 70, a 2D plain image or the like is displayed on the display unit 58 rather than a 3D reconstructed image in the cine-display mode. In case that there are switching instructions from the switching determiner 70 after a 2D plain image or the like has been displayed, the cine-display mode is resumed. In other words, according to the first control process, a 2D plain image is forcibly inserted and displayed on the display unit 58 during the cine-display mode.

(2) Second Control Process

First, a plain image is displayed on the screen of the display unit 58. Thereafter, a 3D reconstructed image, instead of the plain image, is displayed in the cine display mode. The display control process subsequent to the starting of the cine display mode is carried out in the same way as in the first control process.

(3) Third Control Process

The display controller 68 presets a display sequence for displaying tomographic images and plain images on the display unit 58, so that a plain image will be inserted and displayed per each of a prescribed number of tomographic images on the display unit 58. In this manner, respective images can be read from the image memory 62 and displayed on the display unit 58 according to the preset display sequence. In case that there are switching instructions from the switching determiner 70 while the display on the display unit 58 is temporarily canceled, then an image of a different kind may be displayed on the display unit 58, instead of the image that was displayed on the display unit 58 immediately before the display thereof was canceled.

More specifically, in case that a tomographic image has been displayed on the display unit 58 immediately before the display was canceled, then a plain image is displayed instead of the tomographic image. On the other hand, in case that a plain image has been displayed on the display unit 58 immediately before the display was canceled, then a tomographic image is displayed instead of the plain image. Further, in case that there are switching instructions from the switching determiner 70 after switching between the images, the display according to the aforementioned display sequence is resumed. Consequently, according to the third control process, a 2D plain image also is forcibly inserted and displayed on the display unit 58 during the cine-display mode.

(4) Fourth Control Process

In case that image display data representing a plain image inserted per each of a prescribed number of tomographic images according to the display sequence described above have been generated by the image processor 66 and stored in the image memory 62, then the display controller 68 reads the image display data from the image memory 62, and controls the display unit 58 to display the read image display data. In case that there are switching instructions from the switching determiner 70 while the display on the display unit 58 is temporarily canceled, then an image of a different kind may be displayed on the display unit 58 instead of the image that has been displayed on the display unit 58 immediately before the display was canceled. Further, in case that there are switching instructions from the switching determiner 70 after switching between the images, then display of the image display data is resumed.

Inasmuch as tomographic images and plain images also are stored in the server 16, the image processor 66 may generate image display data using the tomographic images and the plain images that are stored in the server 16, rather than generating image display data using the tomographic images and the plain images that are stored in the image memory 62.

Processing that takes place subsequent to step S12 represents details of the first through fourth control processes described above. The first through fourth control processes will be described in sequence below.

[First Control Process]

Initially, the first control process will be described below.

In case that the display controller 68 selects the first control process in step S11, then in the following step S12, the display controller 68 reads respective tomographic images from the image memory 62, and successively outputs the read respective tomographic images to the display unit 58. Consequently, a 3D reconstructed image starts to be displayed in the cine-display mode (the respective tomographic images start to be displayed successively) on the screen of the display unit 58.

According to the first control process, the cine-display mode covers a case in which the display controller 68 automatically and successively reads respective tomographic images from the image memory 62, and displays the tomographic images on the display unit 58, as well as a case in which the display controller 68 controls the display unit 58 to successively display tomographic images each time that the doctor operates the input operating unit 56, such as a mouse wheel or the like, while viewing the tomographic images that are displayed on the display unit 58, after having controlled the display unit 58 to display a tomographic image (e.g., a first tomographic image) at the initial sectional position.

In step S13, in case that the doctor spots an irregularity (target) such as a lesion or the like that the doctor is concerned about while viewing a tomographic image at any sectional position thereof, the doctor operates the input operating unit 56 in order to instruct the display controller 68 to cancel the cine-display mode (step S13: YES). According to instructions from the input operating unit 56, the display controller 68 cancels the cine-display mode.

In step S14, the switching determiner 70 determines whether or not to switch the displayed image on the display unit 58. Since the switching determiner 70 has received instructions from the input operating unit 56, the switching determiner 70 determines whether to immediately switch the displayed image on the display unit 58, or to switch the displayed image on the display unit 58 after the elapse of a predetermined time (step S14: YES). In addition, the switching determiner 70 sends the determined result, which represents switching instructions, to the display controller 68. Whether to immediately switch the displayed image on the display unit 58 or to switch the displayed image on the display unit 58 after the elapse of a predetermined time may be determined, for example, depending on whether or not the doctor is capable of perceiving the tomographic image as an afterimage.

In step S15, instead of the cine-display mode, the display controller 68 displays a plain image on the screen of the display unit 58, according to the determined result sent from the switching determiner 70.

Figure 7B:
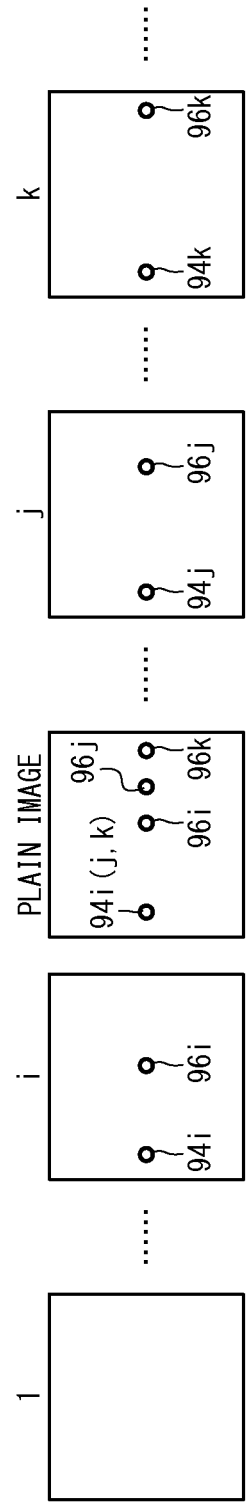
FIG. 7B is a diagram showing a manner in which the plain image shown in FIG. 6B is inserted between certain ones of the tomographic images displayed in the cine-display mode shown in FIG. 7A.

FIG. 7B shows by way of example the manner in which a plain image is displayed after an ith tomographic image has been displayed during the cine-display mode.

In this case, the doctor views the ith tomographic image, judges that the targets 94$i$, 96$i$ are irregularities such as lesions or the like that the doctor is concerned about, and operates the input operating unit 56 in order to cancel the cine-display mode. Thereafter, the display unit 58 displays a plain image instead of the ith tomographic image. The tomographic images including the ith tomographic image and the plain image are displayed at essentially the same scale on the screen of the display unit 58.

Even though the display on the display unit 58 switches to the plain image, the doctor perceives the ith tomographic image as an afterimage immediately before the display switches (immediately before the cine-display mode is canceled). In addition, since the ith tomographic image and the plain image are displayed at essentially the same scale on the screen of the display unit 58, the doctor is capable of comparing the ith tomographic image and the plain image with each other due to the afterimage effect that occurs with respect to the ith tomographic image.

Since the plain image includes three overlapping targets 94$i$ through 94$k$, the plain image seemingly includes four targets (three targets 96$i$ through 96$k$ and one target 94$i$). Accordingly, by comparing the plain image and the ith tomographic image that is caused by the afterimage effect, the doctor is capable of grasping with ease that two of the four targets are the two targets 94$i$, 96$i$ included within the ith tomographic image.

Thereafter, in case that the doctor operates the input operating unit 56 in order to instruct the display controller 68 to resume the cine-display mode (step S16: YES), the display controller 68 resumes the cine-display mode according to instructions from the input operating unit 56 (step S17). Since the screen of the display unit 58 switches from displaying the plain image to displaying the cine-display mode, the doctor perceives the plain image as an afterimage.

As a result, on account of the afterimage effect, the doctor is capable of comparing the jth tomographic image and the plain image with each other, and can also compare the kth tomographic image and the plain image with each other by viewing the jth tomographic image and the kth tomographic image. Therefore, the doctor can easily grasp that two of the targets in the plain image are the two targets 94$j$, 96$j$ included within the jth tomographic image, and that two of the targets in the plain image are the two targets 94$k$, 96$k$ included within the kth tomographic image. In addition, the doctor can grasp that the left target in the plain image is included as three overlapping targets 94$i$ through 94$k$ that are disposed in mutually different sectional positions.

In the first control process, the plain image may be displayed immediately after display of the jth tomographic image and/or the kth tomographic image. In this case, the processes of steps S13 through S17 may be repeated. In this manner, on account of the afterimage effect, it is possible to efficiently compare the jth tomographic image and the plain image with each other, and also to compare the kth tomographic image and the plain image with each other.

In step S15, rather than only a plain image, a plain image, a tomographic image, and a plain image may be displayed in succession. In this case, the tomographic image should desirably be the tomographic image that was displayed immediately before the cine-display mode was canceled. Inasmuch as a tomographic image, a plain image, a tomographic image, and a plain image, including the tomographic image displayed immediately before the cine-display mode was canceled, are successively displayed on the screen of the display unit 58 due to the afterimage effect, the doctor can easily compare a tomographic image and a plain image with each other, and can quickly extract and confirm targets.

[Second Control Process]

Next, the second control process will be described.

In case that the display controller 68 selects the second control process in step S11, then in step S18, the display controller 68 reads a plain image from the image memory 62, and outputs the read plain image to the display unit 58, so that the plain image is displayed on the screen of the display unit 58.

Thereafter, in the same manner as in the first control process, processing from step S12 is carried out.

According to the second control process, therefore, after a 2D plain image is displayed, the cine-display mode is started, so that the doctor views tomographic images after having perceived the plain image as an afterimage. Therefore, due to the afterimage effect, the doctor can efficiently compare a tomographic image and a plain image with each other, and can quickly extract and confirm targets.

[Third Control Process]

Next, the third control process will be described.

In case that the display controller 68 selects the third control process in step S11, the display controller 68 presets a display sequence for actually displaying images on the display unit 58, with respect to respective tomographic images and plain images that are stored in the image memory 62. More specifically, the display controller 68 presets a display sequence such that a plain image is inserted per each of a prescribed number of tomographic images in the cine-display mode.

In the following step S19, the display controller 68 reads respective tomographic images and plain images from the image memory 62 according to the preset display sequence, and successively displays the respective tomographic images and the plain images on the display unit 58. As a result, on the screen of the display unit 58, a sequence of tomographic images and plain images are displayed in a sequence of a prescribed number of tomographic images in the cine-display mode, a single plain image, a prescribed number of tomographic images in the cine-display mode, a single plain image, . . . .

According to the third control process, the cine-display mode also covers a case in which the display controller 68 automatically and successively reads images from the image memory 62, and displays the respective images on the display unit 58 according to the display sequence, as well as a case in which the display controller 68 controls the display unit 58 to display tomographic images or a plain image according to the display sequence each time that the doctor operates the input operating unit 56, such as a mouse wheel or the like, while viewing the tomographic images displayed on the display unit 58, after having controlled the display unit 58 to display an initial tomographic image (e.g., the first tomographic image).

In step S20, in the same manner as in step S13, in a case where the doctor spots an irregularity (target) such as a lesion or the like that the doctor is concerned about while viewing a tomographic image at any sectional position thereof or any plain image, the doctor operates the input operating unit 56 in order to instruct the display controller 68 to cancel the cine-display mode (step S20: YES). According to the instructions from the input operating unit 56, the display controller 68 cancels the cine-display mode.

In the following step S21, in the same manner as in step S14, the switching determiner 70 determines whether or not to switch the displayed image on the display unit 58. Since the switching determiner 70 has received instructions from the input operating unit 56, the switching determiner 70 determines whether to immediately switch the displayed image on the display unit 58, or to switch the displayed image on the display unit 58 after the elapse of a predetermined time (step S21: YES). The switching determiner 70 sends the determined result, which represents switching instructions, to the display controller 68.

In step S22, according to the determined result from the switching determiner 70, the display controller 68 controls the display unit 58 in order to display on the screen of the display unit 58 an image, which is different in kind from the image that was displayed immediately before the cine-display mode was canceled, instead of the image that was displayed immediately before the cine-display mode was canceled.

More specifically, in case that the cine-display mode has been carried out immediately before being canceled, then the display controller 68 controls the display unit 58 in order to display a plain image on the screen, instead of the tomographic image that was displayed immediately before the cine-display mode was canceled. Further, in case that a plain image has been displayed immediately before the cine-display mode was canceled, then the display controller 68 controls the display unit 58 in order to display tomographic images on the screen, instead of the plain image that was displayed immediately before the cine-display mode was canceled.

In this case, since the doctor perceives the image immediately before the cine-display mode was canceled as an afterimage, due to the afterimage effect, the doctor can efficiently compare the image immediately before the cine-display mode was canceled and the image after the display has been switched with each other, and can quickly extract and confirm targets.

In order to resume the cine-display mode in the third control process, the processes of steps S16 and S17 may be performed.

In the third control process, in case that canceling the display of an image and switching from an image are carried out a plurality of times, then the processes of steps S19 through S22 and the processes of steps S16 and 17 may be repeated.

In step S22, in the same manner as in step S15, in case that the cine-display mode has been carried out immediately before being canceled, then the display controller 68 may control the display unit 58 to display on the screen a sequence of a plain image, a tomographic image, and a plain image, instead of the tomographic image that was displayed before the cine-display mode was canceled. Further, in case that a plain image has been displayed immediately before the cine-display mode was canceled, the display controller 68 may control the display unit 58 to display on the screen a sequence of a tomographic image (a tomographic image that is displayed one prior to a plain image), a plain image, and a tomographic image, instead of the plain image that was displayed immediately before the cine-display mode was canceled. In either case, the doctor can easily compare the tomographic image and the plain image with each other due to an afterimage effect, and can quickly extract and confirm targets.

[Fourth Control Process]

Next, the fourth control process will be described.

In case that the display controller 68 selects the fourth control process in step S11, the display controller 68 reads image display data that is stored in the image memory 62, and in step S19, outputs the read image display data to the display unit 58, thereby controlling the display unit 58 to automatically display on the screen a sequence of tomographic images and plain images, according to a sequence of a prescribed number of tomographic images in the cine-display mode, a single plain image, a prescribed number of tomographic images in the cine-display mode, a single plain image, . . . .

Thereafter, the processes from step S20 are carried out in the same manner as in the third control process.

Therefore, according to the fourth control process, since it is unnecessary for the display controller 68 to preset a display sequence, unlike in the third control process, a prescribed number of tomographic images and a single plain image can automatically be displayed simply by outputting the image display data to the display unit 58.

[Display Control Process Carried Out by the Viewer 18]

The above operations have been described as principally being performed by the console 14. However, in case that the above operations are carried out by the viewer 18, the description of the above operations may be modified in the following manner.

Respective structural components of the console 14 are replaced with respective components of the viewer 18.

Since the viewer 18 does not include the image capturing condition setting section 60, only the processes of steps S6, S7, and S10 through S22 are carried out.

The viewer 18 is connected to the mammographic apparatus 12 through the console 14, and therefore, the viewer 18 receives projected images and plain images from the mammographic apparatus 12 through the console 14.

[Advantages of the Present Embodiment]

According to the present embodiment, as described above, assuming that the display unit 58, 78 is capable of displaying a plurality of tomographic images or at least one plain image of the breast 22, the display controller 68, 88 switches between the display of a sequence of respective tomographic images (the display of a 3D reconstructed image in the cine-display mode) or the display of a plain image on the display unit 58, 78.

Owing thereto, on the screen of the display unit 58, 78, the cine-display mode switches to the display of a plain image, or the display of a plain image switches to the cine-display mode at any desired timing. Consequently, according to the present embodiment, the respective tomographic images and the plain image are not displayed simultaneously on the same screen, thereby making it possible to display the respective tomographic images and the plain image for comparison on one screen.

Immediately after the display on the screen has switched, due to an afterimage effect, the doctor perceives the image that was displayed immediately before switching of the display as remaining. Therefore, in a case where the doctor views an image displayed on the screen immediately after switching of the display, the doctor is capable of comparing the image and the image immediately before switching of the display, which is perceived due to an afterimage effect.

Therefore, the doctor is capable of comparing a 2D plain image and a 3D reconstructed image (tomographic images) with each other without moving the face or the eyes, and thus the doctor is subjected to a reduced working burden. The doctor also can easily extract irregularities (targets) on the basis of the difference (differential) between the image displayed immediately before switching of the display, and the image displayed immediately after switching of the display. More specifically, the doctor is able to easily identify irregularities (targets) and to pay attention to that which is included within a plain image, as to which tomographic image the irregularities are included in, which sectional position the irregularities exist in, and what the shape and concentration of the irregularities are, etc.

The doctor can also operate the input operating unit 56, 76 in order to cancel the display (e.g., the cine-display mode) on the display unit 58, 78. More specifically, based on instructions from the input operating unit 56, 76, the display controller 68, 88 temporarily cancels the display on the display unit 58, 78, and the switching determiner 70, 90 determines whether to switch the display on the display unit 58, 78 that has been temporarily canceled by the display controller 68, 88. Based on the determined result from the switching determiner 70, 90, the display controller 68, 88 controls the display unit 58, 78. Therefore, using the input operating unit 56, 76, the doctor can instruct the display controller 68, 88 to cancel the display on the display unit 58, 78, and to switch the display at any desired timing.

In response to instructions from the input operating unit 56, 76, the switching determiner 70, 90 may determine to switch the display on the display unit 58, 78 immediately, or to switch the display on the display unit 58, 78 after the elapse of a predetermined time. In either case, in response to instructions from the input operating unit 56, 76, the switching determiner 70, 90 can perform a determining process for switching the display on the display unit 58, 78 at any appropriate timing. The display controller 68, 88 can also switch the display on the display unit 58, 78 at an appropriate timing in accordance with the switching determiner 70, 90.

The display controller 68, 88 controls the display unit 58, 78 in order to display an image that is different in kind from the image that has been displayed on the display unit 58, 78 immediately before the display was canceled, instead of the image displayed on the display unit. Therefore, it is possible to efficiently switch from the cine-display mode to the display of a plain image, or from the display of a plain image to the cine-display mode.

In case that a tomographic image has been displayed on the display unit 58, 78 immediately before the display was canceled, then the display controller 68, 88 may control the display unit 58, 78 to display a sequence of a plain image, a tomographic image, and a plain image in that order. Thus, the doctor is able to compare the plain image and the tomographic image with each other due to an afterimage effect, and can efficiently ascertain whether or not targets that correspond to targets included within the tomographic image (afterimage) exist in the plain image, and can confirm how such corresponding targets are included within the plain image. In other words, the doctor can easily make a comparative observation as to how targets that are found in a tomographic image are included within a plain image, and what the shape and concentration of the targets are.

On the other hand, in case that a plain image has been displayed on the display unit 58, 78 immediately before the display was canceled, then the display controller 68, 88 may control the display unit 58, 78 to display a sequence of a tomographic image, a plain image, and a tomographic image in that order. Thus, the doctor is able to compare the plain image and the tomographic image with each other due to an afterimage effect, and can efficiently ascertain whether or not targets that correspond to targets included within the plain image (afterimage) exist in the tomographic image or not, and can confirm how such corresponding targets are included within the tomographic image. In other words, the doctor can easily make a comparative observation as to how targets that are found in a plain image are included within a tomographic image, and what the shape and concentration of the targets are.

Using a tomographic image, which is displayed in a preceding order to a plain image that is displayed on the display unit 58, 78 immediately before the display is canceled, the display controller 68, 88 may control the display unit 58, 78 in order to display a sequence of the tomographic image, a plain image, and a tomographic image after the display is canceled. Accordingly, it is possible to more efficiently display a plain image and a tomographic image for comparison, and to search for and confirm targets within the tomographic image.

In case that the display unit 58, 78 is operated in the cine-display mode, the display controller 68, 88 may control the display unit 58, 78 to display a plain image each time that the display unit 58, 78 successively displays a prescribed number of tomographic images. Consequently, the screen of the display unit 58, 78 automatically switches between tomographic images and a plain image each time that a prescribed number of tomographic images have been displayed. As a result, the doctor can more efficiently compare a tomographic image and a plain image with each other and extract targets. In other words, the doctor can efficiently make a comparative observation as to how targets that are found in a tomographic image are included within a plain image, and can make a comparative observation as to how targets that are found in a plain image are included within a tomographic image.

The display controller 68, 88 may display images in the cine-display mode on the display unit 58, 78, using image display data representing a plain image inserted per each of a prescribed number of tomographic images. Therefore, the display controller 68, 88 can easily control switching of the display on the display unit 58, 78. The image display data may be generated in advance.

Since the display controller 68, 88 controls the display unit 58, 78 to display tomographic images and a plain image at essentially the same scale, any movement of the face and eyes of the doctor can be reduced, so that the doctor is subjected to a reduced working burden. Further, since the images are displayed in the same scale, the doctor is capable of easily comparing targets such as lesions or the like to which attention should be focused on in the plain image and in the tomographic images, as to what size and concentration the targets have.

The display controller 68, 88 may control the display unit 58, 78 in order to display tomographic images in the cine-display mode after having controlled the display unit 58, 78 to display a plain image. Therefore, after the doctor has extracted targets that are included within the plain image by viewing the plain image, the doctor can confirm whether or not a tomographic image exists that includes the extracted targets by viewing the tomographic images.

The present invention is not limited to the embodiment described above, but various arrangements may be employed therein without departing from the scope of the invention as set forth in the appended claims.

The invention claimed is:

1. An image display apparatus comprising:
   a display unit capable of displaying a plurality of tomographic images or at least one plain image of a target object;
   a switching determiner configured to determine whether to switch the display on the display unit; and
   a display controller configured to control the display unit;
   wherein the display controller is capable of switching the display on the display unit to the display of tomographic images in sequence or to the display of a plain image,
   in case that the switching determiner determines to switch the display on the display unit, the display controller controls the display unit to display an image, which is different in kind from the image displayed on the display unit, instead of the image displayed on the display unit,
   in case that the plain image is displayed on the display unit, the display controller controls the display unit to display a sequence of a tomographic image, a plain image, and a tomographic image, instead of the plain image displayed on the display unit, using a tomographic image, which is displayed in a preceding order to the plain image displayed on the display unit,
   wherein in case that the display controller controls the display unit to display tomographic images in sequence, the display controller controls the display unit to display a plain image each time that the display unit displays a prescribed number of tomographic images in sequence.

2. The image display apparatus according to claim 1, further comprising:
   a cancellation instructing unit configured to instruct the display controller to cancel the display on the display unit;
   wherein the display controller cancels the display on the display unit in response to instructions from the cancellation instructing unit; and
   the switching determiner determines whether or not to switch the display on the display unit that has been canceled by the display controller.

3. The image display apparatus according to claim 1, wherein the display controller controls the display unit to display tomographic images in sequence, using data representing a plain image that is inserted per each of a prescribed number of tomographic images.

4. The image display apparatus according to claim 1, wherein the display controller controls the display unit to display the tomographic images and the plain image at substantially the same scale.

5. The image display apparatus according to claim 1, wherein the display controller controls the display unit to display the tomographic images in sequence after having controlled the display unit to display the plain image.

6. The image display apparatus according to claim 1, wherein the tomographic images are displayed sequentially in a cine-display mode.

7. An image display method in which a display unit is capable of displaying a plurality of tomographic images or at least one plain image of a target object, comprising:
   determining, with a switching determiner, whether to switch the display on the display unit;
   switching, with a display controller, the display on the display unit to the display of tomographic images in sequence or to the display of a plain image,
   wherein in case that the switching determiner determines to switch the display on the display unit, the display controller controls the display unit to display an image, which is different in kind from the image displayed on the display unit, instead of the image displayed on the display unit,
   in case that the plain image is displayed on the display unit, the display controller controls the display unit to display a sequence of a tomographic image, a plain image, and a tomographic image, instead of the plain image displayed on the display unit, using a tomographic image, which is displayed in a preceding order to the plain image displayed on the display unit,
   wherein in case that the display controller controls the display unit to display tomographic images in sequence, the display controller controls the display unit to display a plain image each time that the display unit displays a prescribed number of tomographic images in sequence.

8. A medical image diagnosing apparatus comprising:
   a tomographic image generator configured to generate a plurality of tomographic images using a plurality of projected images captured of a target object;

a display unit that is capable of displaying the tomographic images or at least one plain image captured of the target object;
a switching determiner configured to determine whether to switch the display on the display unit; and
a display controller configured to control the display unit;
wherein the display controller is capable of switching the display on the display unit to the display of tomographic images in sequence or to the display of a plain image,
in case that the switching determiner determines to switch the display on the display unit, the display controller controls the display unit to display an image, which is different in kind from the image displayed on the display unit, instead of the image displayed on the display unit,
in case that the plain image is displayed on the display unit, the display controller controls the display unit to display a sequence of a tomographic image, a plain image, and a tomographic image, instead of the plain image displayed on the display unit, using a tomographic image, which is displayed in a preceding order to the plain image displayed on the display unit,
wherein in case that the display controller controls the display unit to display tomographic images in sequence, the display controller controls the display unit to display a plain image each time that the display unit displays a prescribed number of tomographic images in sequence.

9. A medical image diagnosing method comprising:
generating, with a tomographic image generator, a plurality of tomographic images using a plurality of projected images captured of a target object,
wherein a display unit is capable of displaying a plurality of tomographic images or at least one plain image of a target object;
determining, with a switching determiner, whether to switch the display on the display unit; and
switching, with a display controller, a display on the display unit to the display of tomographic images in sequence or to the display of a plain image,
wherein in case that the switching determiner determines to switch the display on the display unit, the display controller controls the display unit to display an image, which is different in kind from the image displayed on the display unit, instead of the image displayed on the display unit,
in case that the plain image is displayed on the display unit, the display controller controls the display unit to display a sequence of a tomographic image, a plain image, and a tomographic image, instead of the plain image displayed on the display unit, using a tomographic image, which is displayed in a preceding order to the plain image displayed on the display unit,
wherein in case that the display controller controls the display unit to display tomographic images in sequence, the display controller controls the display unit to display a plain image each time that the display unit displays a prescribed number of tomographic images in sequence.

10. A medical image diagnosing system comprising:
an image capturing apparatus configured to acquire a plurality of projected images captured of a target object and at least one plain image captured of the target object; and
a medical image diagnosing apparatus configured to acquire the projected images and the plain image from the image capturing apparatus;
the medical image diagnosing apparatus comprising
a tomographic image generator configured to generate a plurality of tomographic images using the projected images,
a display unit capable of displaying the tomographic images or the plain image,
a switching determiner configured to determine whether to switch the display on the display unit, and
a display controller configured to control the display unit;
wherein the display controller is capable of switching the display on the display unit to the display of tomographic images in sequence or to the display of a plain image,
in case that the switching determiner determines to switch the display on the display unit, the display controller controls the display unit to display an image, which is different in kind from the image displayed on the display unit, instead of the image displayed on the display unit,
in case that the plain image is displayed on the display unit, the display controller controls the display unit to display a sequence of a tomographic image, a plain image, and a tomographic image, instead of the plain image displayed on the display unit, using a tomographic image, which is displayed in a preceding order to the plain image displayed on the display unit,
wherein in case that the display controller controls the display unit to display tomographic images in sequence, the display controller controls the display unit to display a plain image each time that the display unit displays a prescribed number of tomographic images in sequence.

11. A data generating apparatus in which a display controller is capable of displaying a plurality of tomographic images or at least one plain image of a target object on a display unit, and a switching determiner determines whether to switch the display on the display unit, comprising:
a data generator configured to generate data representing a plain image that is inserted per each of a prescribed number of tomographic images;
wherein in case that the display controller is supplied with the data, the display controller switches the display on the display unit to the display of tomographic images in sequence or to the display of a plain image, based on the data,
in case that the switching determiner determines to switch the display on the display unit, the display controller controls the display unit to display an image, which is different in kind from the image displayed on the display unit, instead of the image displayed on the display unit,
in case that the plain image is displayed on the display unit, the display controller controls the display unit to display a sequence of a tomographic image, a plain image, and a tomographic image, instead of the plain image displayed on the display unit, using a tomographic image, which is displayed in a preceding order to the plain image displayed on the display unit.

12. A data generating method in which a display controller is capable of displaying a plurality of tomographic images or at least one plain image of a target object on a display unit, and a switching determiner determines whether to switch the display on the display unit, comprising:

generating, with a data generator, data representing a plain image that is inserted per each of a prescribed number of tomographic images; and supplying the display controller with the data, such that based on the data, the display controller is made to switch the display on the display unit to the display of tomographic images in sequence or to the display of a plain image, wherein in case that the switching determiner determines to switch the display on the display unit, the display controller controls the display unit to display an image, which is different in kind from the image displayed on the display unit, instead of the image displayed on the display unit, in case that the plain image is displayed on the display unit, the display controller controls the display unit to display a sequence of a tomographic image, a plain image, and a tomographic image, instead of the plain image displayed on the display unit, using a tomographic image, which is displayed in a preceding order to the plain image displayed on the display unit.

13. A non-transitory recording medium storing a program for enabling a computer to function as:

a display unit capable of displaying a plurality of tomographic images or at least one plain image of a target object;

a switching determiner configured to determine whether to switch the display on the display unit; and a display controller configured to switch the display on the display unit to the display of tomographic images in sequence or to the display of a plain image, wherein in case that the switching determiner determines to switch the display on the display unit, the display controller controls the display unit to display an image, which is different in kind from the image displayed on the display unit, instead of the image displayed on the display unit, in case that the plain image is displayed on the display unit, the display controller controls the display unit to display a sequence of a tomographic image, a plain image, and a tomographic image, instead of the plain image displayed on the display unit, using a tomographic image, which is displayed in a preceding order to the plain image displayed on the display unit, wherein in case that the display controller controls the display unit to display tomographic images in sequence, the display controller controls the display unit to display a plain image each time that the display unit displays a prescribed number of tomographic images in sequence.

* * * * *